United States Patent
Brazeau et al.

(10) Patent No.: US 6,789,413 B2
(45) Date of Patent: Sep. 14, 2004

(54) METHOD AND APPARATUS FOR MEASURING EFFECTS OF EXHAUST GAS RECIRCULATION DEPOSITS

(75) Inventors: Craig Brazeau, Hilliard, OH (US); James Robinson, Marysville, OH (US); Andrew Fairchild, Delaware, OH (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/762,010

(22) Filed: Jan. 21, 2004

(65) Prior Publication Data

US 2004/0149009 A1 Aug. 5, 2004

Related U.S. Application Data

(62) Division of application No. 10/121,222, filed on Apr. 12, 2002, now Pat. No. 6,739,184.

(51) Int. Cl.$^7$ ............................................. G01M 15/00
(52) U.S. Cl. ...................................... 73/118.1; 73/23.31
(58) Field of Search .......................... 73/23.31, 23.32, 73/116, 117.2, 117.3, 118.1

(56) References Cited

U.S. PATENT DOCUMENTS

| | | | | |
|---|---|---|---|---|
| 3,986,386 A | * | 10/1976 | Beltzer et al. | ............ 73/863.12 |
| 5,408,215 A | * | 4/1995 | Hamburg | .................... 340/439 |
| 5,410,907 A | * | 5/1995 | Strom et al. | ............... 73/23.31 |
| 5,469,731 A | * | 11/1995 | Decker et al. | ............. 73/23.31 |
| 5,492,005 A | | 2/1996 | Homan et al. | |
| 5,693,874 A | | 12/1997 | De La Cruz et al. | |
| 5,907,109 A | | 5/1999 | Tedeschi | |
| 5,918,256 A | * | 6/1999 | Delaney | ..................... 73/23.31 |
| 6,079,251 A | | 6/2000 | Gaultier et al. | |
| 6,148,656 A | * | 11/2000 | Breton | ....................... 73/23.31 |
| 6,387,706 B1 | | 5/2002 | Eden | |
| 6,470,732 B1 | | 10/2002 | Breton | |
| 6,739,184 B2 | * | 5/2004 | Brazeau et al. | ............ 73/118.1 |
| 2003/0033891 A1 | | 2/2003 | Silvis et al. | |
| 2003/0084712 A1 | | 5/2003 | Smith et al. | |

* cited by examiner

Primary Examiner—Eric S. McCall
(74) Attorney, Agent, or Firm—Rankin, Hill, Porter & Clark LLP; Mark E. Duell

(57) ABSTRACT

A method and apparatus for measuring effects of various conditions on deposit build up in an exhaust gas recirculation system. The apparatus includes a testing jig having a main branch, a test branch, and a control branch. The test and control branches are connected, at an inlet and outlet, to the main branch. Each branch includes a flow control valve so that fluid flow through the test branch can be equalized with fluid flow through the control branch. A parameter of interest, such as temperature, oil, or humidity, in the test branch is modified, and the jig is connected to an engine exhaust, and the flows are equalized. Pressures and temperatures at various points in the jig are monitored and, after a predetermined period of time or when a pressure drop is sensed, the test is complete and the deposits in the test branch are compared with those in the control branch to determine the effect of the altered parameter.

8 Claims, 4 Drawing Sheets

METHOD AND APPARATUS FOR MEASURING EFFECTS OF EXHAUST GAS RECIRCULATION DEPOSITS

This is a divisional of application Ser. No. 10/121,222, filed Apr. 12, 2002, now U.S. Pat. No. 6,739,184.

BACKGROUND OF THE INVENTION

1. Field of the Invention

The present invention generally relates to exhaust system testing devices and methods and, more particularly, toward methods and devices for testing exhaust gas recirculation systems.

2. Description of Related Art

In low emission automobiles it is conventional to recirculate a portion of the exhaust back to the intake manifold to be mixed with the incoming air and subsequently returned to the combustion chamber. Such exhaust gas recirculation (EGR) systems work well in reducing some emissions by lowering engine's maximum combustion temperatures.

The prior art has focused on devices for making EGR systems more effective in delivering exhaust gases to the intake manifold, including provision of dedicated valves to control the flow of exhaust gases. Unfortunately, such EGR systems are susceptible to carbon build-up that, over time, reduces their effectiveness. While there exists some theories as to the causes for such carbon build-up, to date there is no effective device for testing different variables to see how they affect the carbon deposition problem.

U.S. Pat. No. 5,693,874 to De La Cruz et al. discloses a test apparatus for determining deposit formation characteristics of fuels. The testing method includes testing engine parts in a heated test chamber where different fuels are sprayed on the test parts to determine deposit characteristics. U.S. Pat. No. 6,079,251 discloses a system and method for analyzing deposit formation or exhaust particulate content. U.S. Pat. No. 5,492,005 to Homan et al. teaches a related system and method.

Accordingly, there exists a need in the art for a method and system for testing EGR systems to determine the effects of variable conditions on the deposition of carbon. There further exists a need in the art for an EGR system experimental testing and measuring system and method.

SUMMARY OF THE INVENTION

The present invention is directed toward a method and system for determining the effects of variable conditions on the deposition of carbon in EGR systems.

In accordance with the present invention, a testing jig is adapted to receive exhaust gas from an engine, and includes a main branch and a plurality of side branches. The plurality of side branches includes at least one test branch and at least one control branch. Each of the plurality of side branches, as well as the main branch, include valves and sensors to permit the flow and conditions in each of the branches to be monitored and controlled.

In further accordance with the invention, the main branch extends generally longitudinally while the side branches are somewhat U-shaped. Each of the side branches is connected to the main branch at a first end and at a second end. Between the connections, the main branch includes a main valve that is used to create a restriction to flow. Similarly, each of the side branches includes a valve near its second end that is used to equalize flow through the side branches.

In accordance with the method of the present invention, the test branch is modified relative to the control branch to introduce one variable. The variable may be temperature, oil, water, fuel additives, oil and engine treatments, alcohol, other combustibles that may be used in place of or in conjunction with gasoline, a flow restriction, a flow enlargement, or any other desired physical parameter. The main branch is connected to the engine exhaust, and the flow rates through the control tube and the main tube are equalized, and the engine is operated at a predetermined rate. The test may be conducted for a predetermined time period or until a predetermined pressure drop is sensed in the control tube. Thereafter, the deposits or coatings in the test branch and the control branch are analyzed and compared to determine the effect of the variables introduced into the test branch.

BRIEF DESCRIPTION OF THE DRAWINGS

These and further features of the invention will be apparent with reference to the following detailed description and drawings, wherein.

DETAILED DESCRIPTION OF THE PREFERRED EMBODIMENTS

Figure 1:
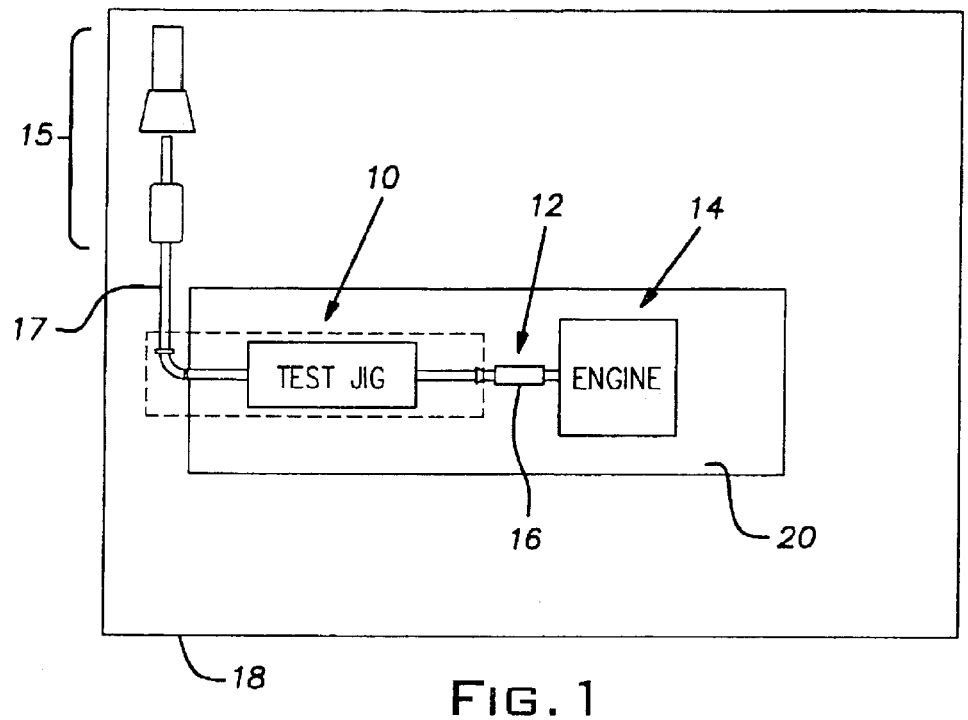
FIG. 1 schematically illustrates a testing system according to the present invention.

With reference to FIG. 1, a testing system according to the present invention is shown. The testing system includes a testing jig 10 that is connected to an exhaust 12 of an automobile engine 14. The engine exhaust 14 includes a catalytic converter 16 that preferably is disposed between the engine 14 and the testing jig 10. However, it is noted that in some circumstances it may be desirable to remove the catalytic converter 16. The testing jig 10 is connected to a downstream exhaust assembly 15 via an exhaust pipe 17. The engine 14 and testing jig 10 are preferably disposed in an environmentally controlled room 18 and the engine 14 is mounted to a dynometer 20, which is well known in the art. The environmentally controlled room 18 permits the engine 14 and testing jig 10 to be operated at a constant temperature in a consistent atmosphere, and will remove random variables from the testing procedure.

Figure 2:
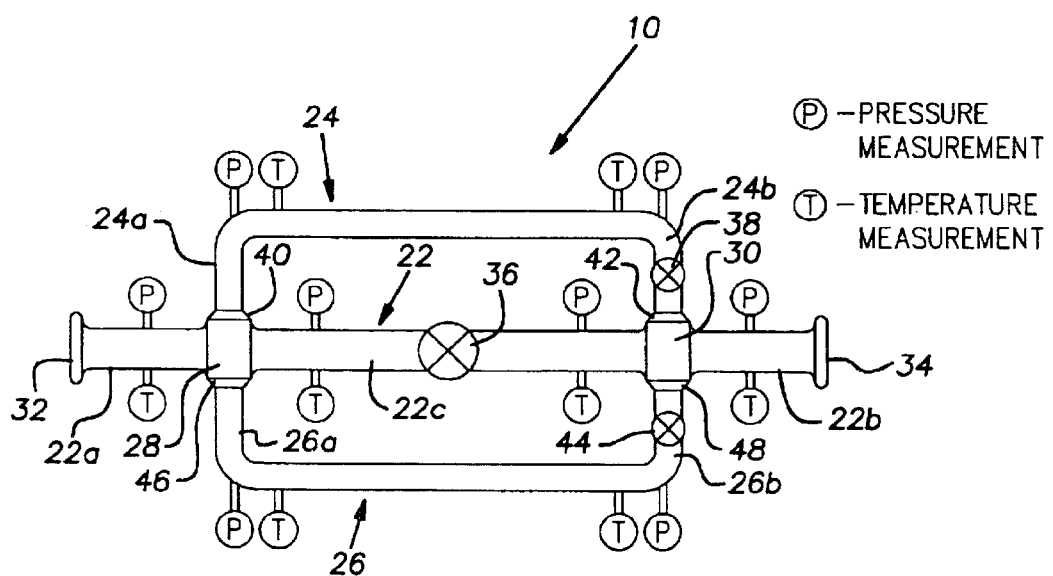
FIG. 2 schematically illustrates a first testing jig according to the present invention.

The testing jig 10 according to a first preferred embodiment is schematically shown in FIG. 2 and includes a main branch 22, a test branch 24, and a control branch 26. The main branch 22 is preferably formed from a material that resists deposits from oxidation, such as 18 CrCb alloy steel, so as to provide a stable platform for several testing procedures. The main branch 22 extends generally longitudinally and defines an inlet section 22a, an outlet section 22b, and a main section 22c. The inlet section 22a is connected to the main section 22c by a first fitting 28, while the main section 22c is connected to the outlet section 22b by a second fitting 30. The first and second fittings 28, 30 also serve to connect the main branch 22 to the test branch 24 and the control branch 26, as will be described more fully hereinafter.

The inlet and outlet sections 22a, 22b include flange-type fittings 32, 34 to facilitate their securement to other portions of the system. For example, the flange-type fitting 32 at the inlet section 22a facilitates attachment to an outlet pipe of the catalytic converter 16, while the flange-type fitting 34 at the outlet section 22b facilitates attachment to the downstream exhaust pipe 17. Further, each of the inlet and outlet sections 22a, 22b includes one or more pressure sensors and temperature sensors to facilitate determination and monitoring of these parameters by a controller (not shown).

The main section 22c of the main branch 22 includes a first valve 36, which is a relatively coarse flow control valve, to regulate fluid flow through the main branch 22. Pressure and temperature sensors are also provided on each side of the first valve 36 in the main branch 22, and permit monitoring of the pressure and temperature within the main section 22c of the main branch 22.

The test branch 24 includes an inlet end 24a, an outlet end 24b, and a second valve 38 adjacent the outlet end 24b. The inlet and outlet ends 24a, 24b include flange-type fittings 40, 42 to facilitate removable attachment to the first and second fittings 28, 30. Pressure and temperature sensors are provided in the test branch 24 to monitor these parameters during a testing procedure. The second valve 38, which is a relatively more precise valve than the first valve 36, is provided to fine-tune flow through the test branch 24, as will be apparent from the following discussion.

The control branch 26 includes an inlet end 26a, an outlet end 26b, and a third valve 44 adjacent the outlet end 26b. The inlet and outlet ends 26a, 26b include flange-type fittings 46, 48 to facilitate removable attachment to the first and second fittings 28, 30. The third valve 44 is essentially identical to the second valve 38 and is provided to fine-tune flow through the control branch 26, as will be apparent from the following discussion. Pressure and temperature sensors are also provided in the control branch 26 to monitor these parameters during the testing procedure.

While the testing branch 24 as described hereinbefore is substantially identical to the control branch 26, a physical condition or parameter of the test branch 24 is modified (or introduced) prior to the testing procedure to determine the effects the modified physical parameter has on deposition or build up within the test branch 24. Such modified physical conditions or parameters may include temperature, oil or water, fuel additives, oil and engine treatments, alcohol, other combustibles that may be used in place of or in conjunction with gasoline, a flow restriction or enlargement, or any other physical variable of interest introduced into the test branch or applied to the test branch.

The testing jig 10 is attached to the engine 14 as shown in FIG. 1. A single parameter or variable, or a combination of plural variables, is altered or introduced into the test branch 24, and then the engine 14 is started. Since the control branch 26 is geometrically and dimensionally identical to the test branch 24, it may be considered apparent that the flow rate through the test branch 24 will be identical to the flow rate through the control branch 26. Preferably, however, the first, second and third valves 36, 38, 44 are adjusted to assure that the flow rate through the control branch 26 is the same as the flow rate through the test branch 24.

The first valve 36 is used to establish a restriction in the test jig 10 and a base flow rate through the test and control branches 24, 26, while the second and third valves 38, 44 are used to fine tune the flows through the test and control branches 24, 26. The flow rate may be detected by a suitable sensor or may be determined by other known methods, such as the pressure method, mass flow, or any other method that provides suitable results.

The testing procedure continues until a predetermined drop in flow rate is detected in the test branch 24 or the control branch 26, or until a predetermined test time has elapsed. The predetermined test time may be, for example, one month of continuous operation. Following the testing procedure, the deposits in the test branch 24 and the control branch 26 are analyzed and compared to determine the effect the modified parameter had on the deposition or build up of coatings on the test branch as compared to the deposits formed in the control branch.

Figure 3:
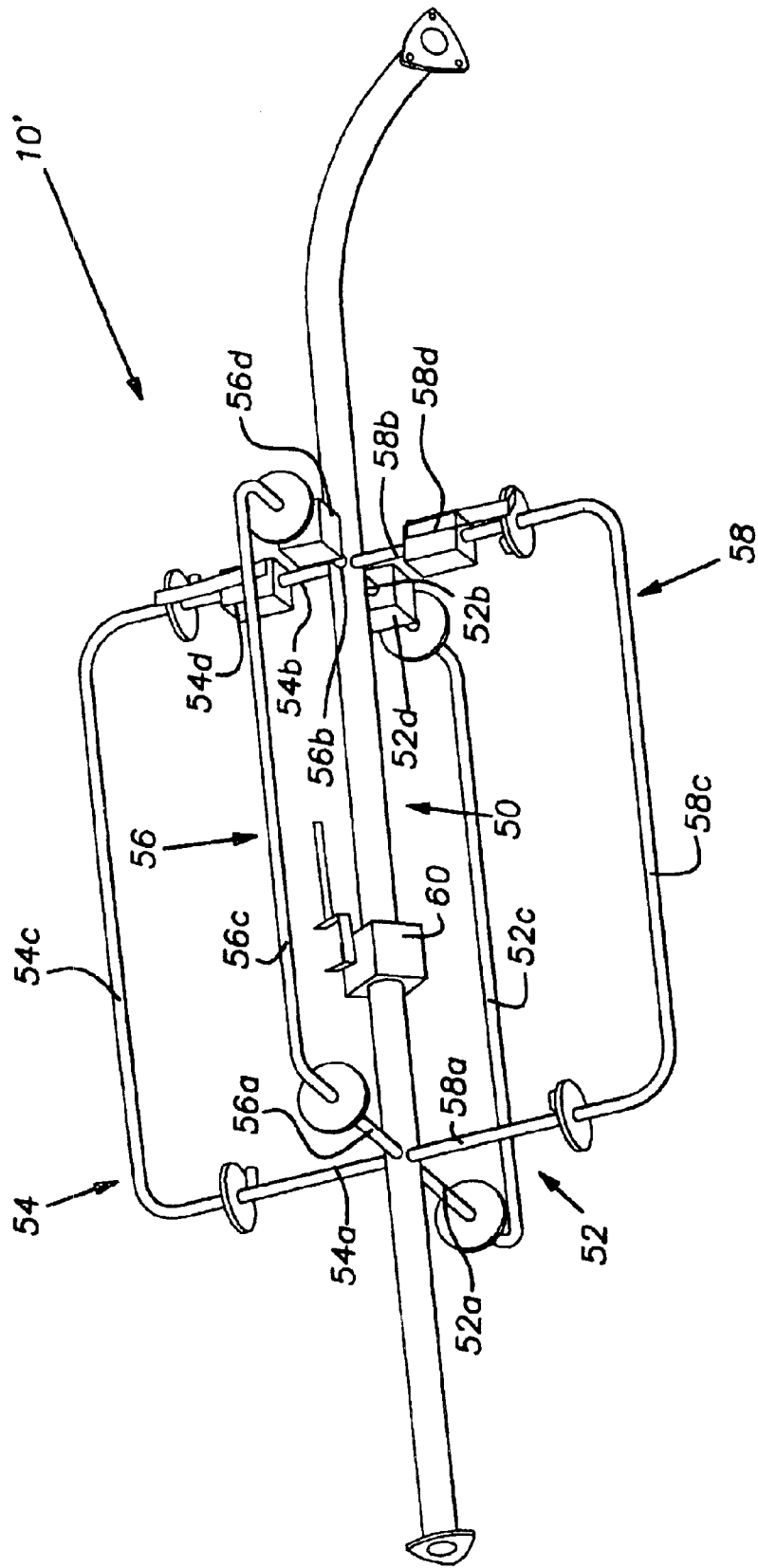
FIG. 3 schematically illustrates a second testing jig according to the present invention.

With reference to FIG. 3, a second embodiment of the testing jig 10' is shown to include a main branch 50, first, second, and third test branches 52, 54, 56, and a control branch 58. As in the first embodiment, the main branch 50 is preferably formed from a material that resists deposits from oxidation, such as 18 CrCb alloy steel, so as to provide a stable platform for several testing procedures. The main branch 50 includes flange-type fittings at each end to permit securing of the testing jig to the engine exhaust and a downstream exhaust pipe (FIG. 1).

Four inlet pipe sections 52a, 54a, 56a, 58a and four outlet pipe sections 52b, 54b, 56b, 58b are fluidly connected to the main branch 50, while a first valve 60 is disposed in the main branch 50 relatively between the inlet pipe sections and outlet pipe sections, as illustrated. Each inlet and outlet pipe section includes a flange-type fitting to which flange-type fittings of an associated test section 52c, 54c, 56c or control section 58c is connected. Accordingly, each test and control branch 52, 54, 56, 58 includes an inlet pipe section 52a, 54a, 56a, 58a, a test/control section 52c, 54c, 56c, 58c, and an outlet pipe section 52b, 54b, 56b, 58b. As will be appreciated, providing flange-type connections between the inlet pipe sections, outlet pipe sections, and test/control section permits interchangeability and compatibility, and facilitates rapid and simplified installation of test/control sections. The inlet and outlet pipe sections 52a, 54a, 56a, 58a; 52b, 54b, 56b, 58b also include temperature and pressure sensor fittings adjacent the flange-type fittings to permit determination of these conditions during the testing procedure. Each of the outlet pipe sections 52b, 54b, 56b, 58b has a fine flow control valve 52d, 54d, 56d, 58d disposed therein to regulate fluid flow through the associated test or control branch.

As in the first embodiment, the first valve 60 is a coarse flow control valve and is used to establish a flow restriction in the test jig 10' and a base flow rate through the test branches 52, 54, 56 and the control branch 58. The fine flow control valves 52d, 54d, 56d, 58d are used to fine-tune and match the flow through the test and control branches.

Accordingly, in the second embodiment, the test and control sections 52c, 54c, 56c, 58c may be manufactured without provision of any special sensor or valve arrangements, reducing the costs associated therewith. Moreover, at least some of the test sections 52c, 54c, 56c may be specially designed to accentuate the parameter being tested. For example, a test section designed to test the effects of temperature may include heating or cooling elements on its exterior surface, as described more fully hereinafter with reference to the third embodiment of the present invention. Moreover, a test section intended to test the effects of fluid substances (i.e., oil, water, fuel additives, oil and engine treatments, alcohol, other combustibles that may be used in place of or in conjunction with gasoline) may be pre-loaded with such substances, or may have metered amounts of such substances introduced therein via suitable ports (not shown) throughout the test procedure. Finally, providing multiple test branches permits several different parameters to be tested in one testing procedure, thereby speeding the collection of comparative data.

Figure 4:
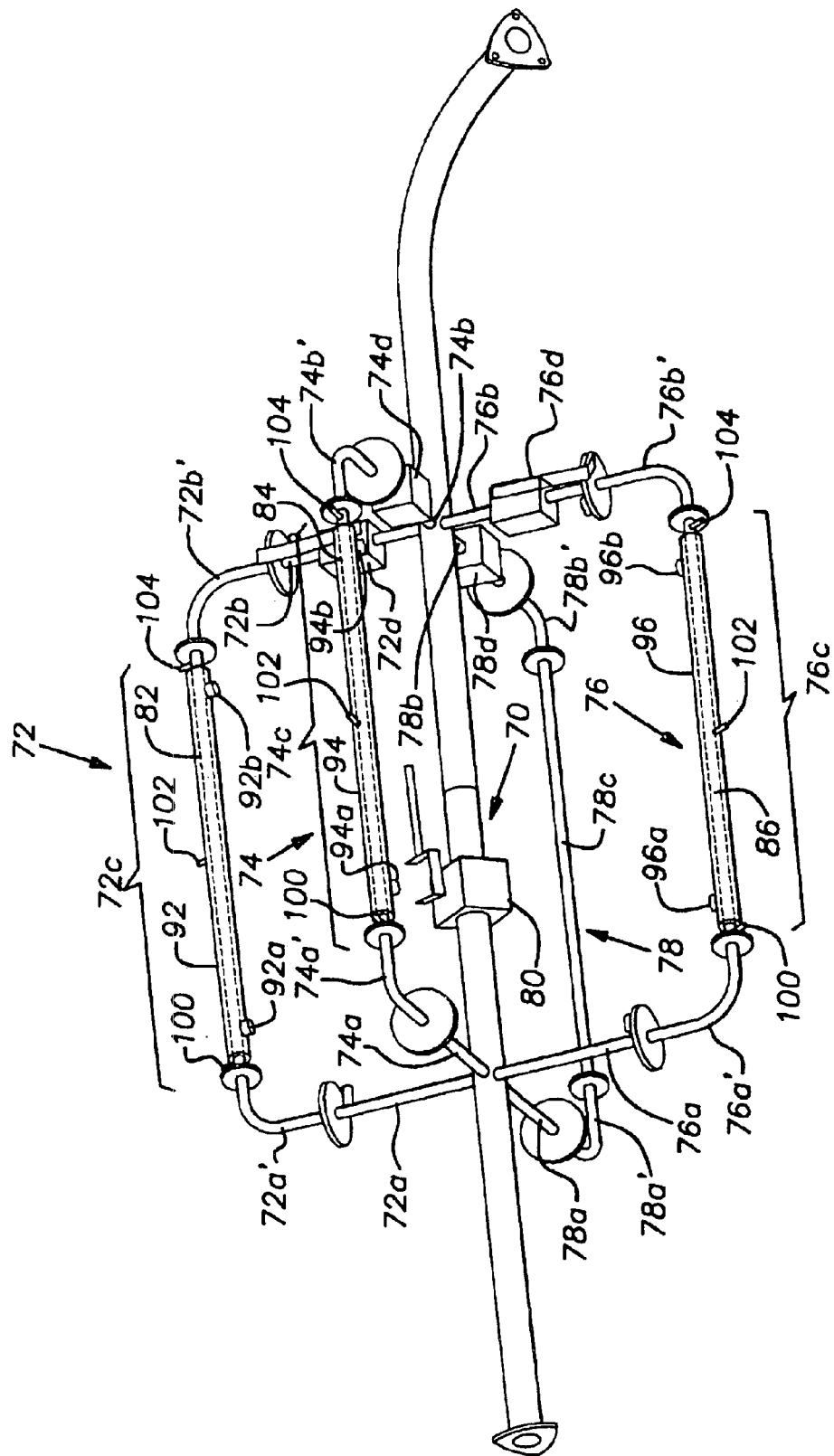
FIG. 4 schematically illustrates a third testing jig according to the present invention; and, FIG. 5 is an end elevational view of the third testing jig shown in FIG. 4.
Figure 5:
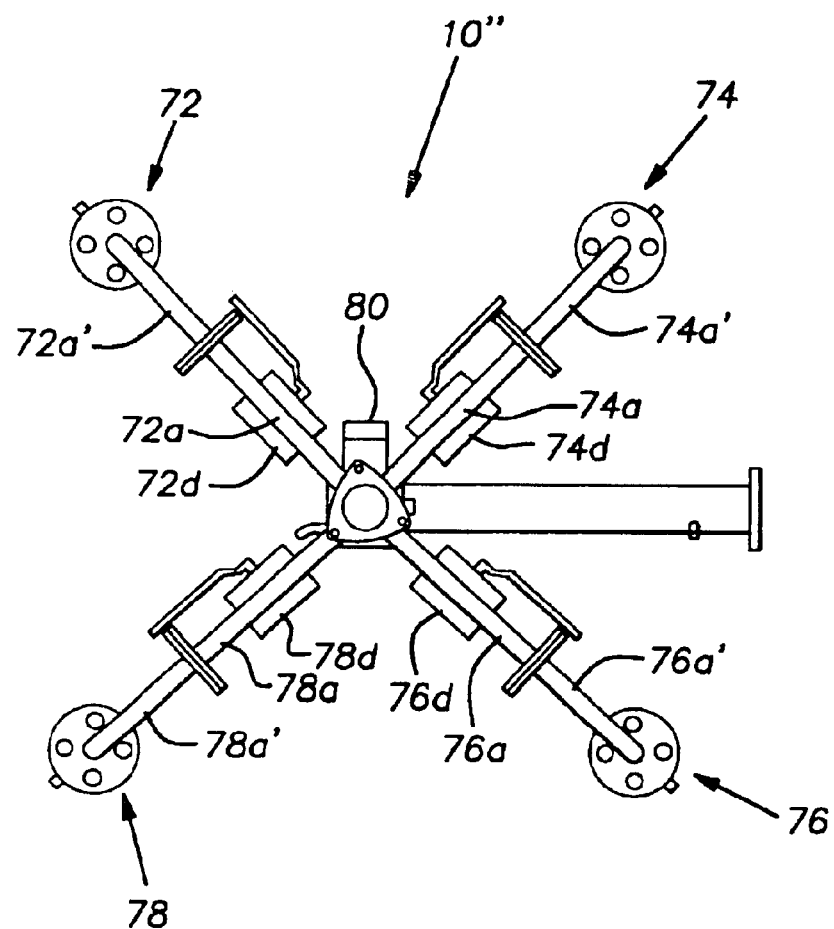

FIGS. 4 and 5 illustrate a third preferred embodiment of the testing jig 10" according to the present invention. The third testing jig 10" includes a main branch 70, first, second, and third test branches 72, 74, 76, and a control branch 78. The main branch 70 is preferably formed from a material that resists deposits from oxidation, such as 18 CrCb alloy steel, so as to provide a stable platform for several testing procedures. The main branch 70 includes flange-type fittings at each end to permit securing of the testing jig 10" to the engine exhaust and a downstream exhaust pipe (FIG. 1). Moreover, the main branch 70 includes a series of temperature sensors and pressure sensors to determine these parameters at multiple locations during each testing procedure.

Four inlet pipe sections 72a, 74a, 76a, 78a and four outlet pipe sections 72b, 74b, 76b, 78b are connected to the main branch 70, while a first valve 80 is disposed in the main branch 70 relatively between the inlet pipe sections and outlet pipe sections, as illustrated. Each inlet and outlet pipe section 72a, 74a, 76a, 78a; 72b, 74b, 76b, 78b includes a flange-type fitting to which associated flange-type fittings of an associated inlet or outlet bend section 72a', 74a', 76a', 78a'; 72b', 74b', 76b', 78b' are secured. A test section 72c, 74c, 76c or control section 78c is secured between an associated inlet and outlet bend section 72a', 74a', 76a', 78a'; 72b', 74b', 76b', 78b', as illustrated. Accordingly, each test or control branch 72, 74, 76, 78 includes an inlet pipe section 72a, 74a, 76a, 78a, an inlet bend section 72a', 74a', 76a', 78a', a test/control section 72c, 74c, 76c, 78c, an outlet bend section 72b', 74b', 76b', 78b', and an outlet pipe section 72b, 74b, 76b, 78b.

The flange-type connections between each section of the test and control branches permits interchangeability and compatibility, and facilitates rapid and simplified installation of the test and control sections. The inlet and outlet pipe sections 72a', 74a', 76a', 78a'; 72b', 74b', 76b', 78b' also include temperature and pressure sensor fittings adjacent the flange-type fittings to permit determination of these conditions during the testing procedures. Moreover, each of the outlet pipe sections 72b', 74b', 76b', 78b' has a fine flow control valve 72d, 74d, 76d, 78d disposed therein to regulate fluid flow through the associated test or control branch 72, 74, 76, 78.

As in the first and second embodiments, the first valve 80 is a coarse flow control valve and is used to establish a flow restriction in the test jig 10" and a base flow rate through the test branches 72, 74, 76 and the control branch 78. The fine flow control valves 72d, 74d, 76d, 78d are used to fine-tune and match the flow through the test and control branches.

The control pipe section 78c consists of a straight section of pipe interconnecting the associated inlet and outlet bend sections 78a', 78b'. Each test pipe section 72c, 74c, 76c includes an inner pipe section 82, 84, 86, essentially identical in length and diameter to the control pipe section 78c, and a surrounding or outer pipe section 92, 94, 96. The outer pipe section 92, 94, 96 surrounds the inner pipe section 82, 84, 86 and has a fluid inlet 92a, 94a, 96a at one end and a fluid outlet 92b, 94b, 96b at the opposite end. Cooling or heating fluid flows through the outer pipe section 92, 94, 96 from the inlet to the outlet and over the inner pipe section 82, 84, 86 and serves to cool or heat the inner pipe section. Accordingly, the outer pipe section serves as a heat exchanger to modify the temperature of the inner pipe section and the exhaust gases flowing therethrough.

A series of thermocouples 100, 102, 104 are provided to monitor the temperature at various locations in the inner pipe section 82, 84, 86. A first thermocouple 100 is provided near the inlet to the inner pipe section 82, 84, 86 to measure the temperature of the exhaust gases entering the heat exchanger. A second thermocouple 102 extends through the outer pipe section 92, 94, 96 and is provided at a midpoint of the inner pipe section 82, 84, 86 to measure the temperature of the inner pipe section within the heat exchanger. Finally, a third thermocouple 14 is provided near an outlet of the inner pipe section 82, 84, 86 to measure temperature immediately downstream the heat exchanger. It is expected that the measurements from the thermocouples will illustrate a gradient of temperatures within each test pipe section 72c, 74c, 76c that can be correlated to deposit formation along the length of the inner test pipe 82, 84, 86.

In addition to the affects of temperature, it is contemplated that the testing jig according to the third embodiment may be used to test the effects of other physical variables in combination with temperature. For example, a temperature modified test branch may further be used to test the effects of oil or water (humidity), fuel additives, oil and engine treatments, alcohol and/or other combustibles that may be used in place of or in conjunction with gasoline and, to that end, may be pre-loaded with such substances, or may have metered amounts of such substances introduced therein throughout the test procedure by means of appropriate injection ports (not shown).

Although the preferred embodiments of the present invention have been described herein with particularity, it is considered apparent that the invention is capable of numerous modifications, replacements, and modifications of parts without departing from the scope and spirit of the present invention. Accordingly, the present invention is not to be limited to the specific embodiments described herein, but rather is only to be defined by the claims appended hereto.

What is claimed is:

1. A method for testing engine exhaust gases to determine the effects of variable parameters on deposit build up in exhaust gas recirculation systems, comprising the steps of:

providing a test jig having a test branch and a control branch;

modifying a parameter of interest in said test branch;

directing exhaust gas from an engine through said test jig for a period of time;

following said period of time, comparing build up on said test branch with build up on said control branch to determine the effect of the modified parameter deposit formation.

2. The method of claim 1, wherein said test jig further comprises a main branch, each of said branches having a control valve disposed therein, comprising the further step of using said control valves to regulate flow through said branches.

3. The method of claim 1, wherein said parameter of interest is selected from the group consisting of oil, water, fuel additives, oil treatments, engine treatments, alcohol, and other combustibles that may be used in place of or in conjunction with gasoline.

4. The method of claim 1, comprising the further steps of analyzing said build up to determine components thereof.

5. The method of claim 2, wherein said parameter of interest is selected from the group consisting of oil water, fuel additives, oil treatments, engine treatments, alcohol, and other combustibles that may be used in place of or in conjunction with gasoline.

6. The method of claim 2, comprising the further steps of analyzing said build up to determine components thereof.

7. The method of claim 3, comprising the further steps of analyzing said build up to determine components thereof.

8. The method of claim 5, comprising the further steps of analyzing said build up to determine components thereof.

* * * * *

UNITED STATES PATENT AND TRADEMARK OFFICE
CERTIFICATE OF CORRECTION

PATENT NO.    : 6,789,413 B2
DATED         : September 14, 2004
INVENTOR(S)   : James Robinson It is certified that error appears in the above-identified patent and that said Letters Patent is hereby corrected as shown below:

Column 6,
Line 61, delete "oil water" and insert therefor -- oil, water --.

Signed and Sealed this

First Day of February, 2005

JON W. DUDAS
*Director of the United States Patent and Trademark Office*